US012797026B2

(12) United States Patent
Chen et al.

(10) Patent No.: US 12,797,026 B2
(45) Date of Patent: Nov. 17, 2026

(54) SYSTEM AND METHOD FOR CONTROLLING ERRORS IN COMPUTED TOMOGRAPHY NUMBER WITHOUT RAW DETECTOR COUNT DATA

(71) Applicant: Wisconsin Alumni Research Foundation, Madison, WI (US)

(72) Inventors: Guang-Hong Chen, Madison, WI (US); Ke Li, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 963 days.

(21) Appl. No.: 17/987,917

(22) Filed: Nov. 16, 2022

(65) Prior Publication Data

US 2024/0164735 A1 May 23, 2024

(51) Int. Cl.

| | |
|---|---|
| ***A61B 6/00*** | (2024.01) |
| ***A61B 6/03*** | (2006.01) |
| ***A61B 6/42*** | (2024.01) |
| ***G06T 12/20*** | (2026.01) |
| ***G06T 12/30*** | (2026.01) |

(52) U.S. Cl.

CPC .............. *A61B 6/5205* (2013.01); *A61B 6/03* (2013.01); *A61B 6/4241* (2013.01); *G06T 12/20* (2026.01); *G06T 12/30* (2026.01); *G06T 2210/41* (2013.01); *G06T 2211/421* (2013.01)

(58) Field of Classification Search

CPC ......... A61B 6/03; A61B 6/032; A61B 6/5205; A61B 6/4241; G06T 11/006; G06T 11/008; G06T 11/005; G06T 2210/41; G06T 2211/40; G06T 2211/421

See application file for complete search history.

(56) References Cited

U.S. PATENT DOCUMENTS

| | | | | |
|---|---|---|---|---|
| 2013/0202080 | A1* | 8/2013 | Yu | A61B 6/583 378/19 |
| 2018/0204306 | A1* | 7/2018 | Brendel | G06T 5/50 |
| 2018/0204356 | A1* | 7/2018 | Xia | A61B 6/032 |
| 2019/0019317 | A1* | 1/2019 | Zhang | A61B 6/582 |

(Continued)

FOREIGN PATENT DOCUMENTS

| | | | | |
|---|---|---|---|---|
| JP | 2003126078 | * | 5/2003 | A61B 6/03 |

OTHER PUBLICATIONS

Chen et al., "Overcoming the challenges of inaccurate CT numbers in low dose CT," in Medical Imaging 2022: Physics of Medical Imaging, W. Zhao and L. Yu, eds., 12031, pp. 276-281, International Society for Optics and Photonics, SPIE, 2022.

(Continued)

*Primary Examiner* — Zhiyu Lu

(74) *Attorney, Agent, or Firm* — Quarles & Brady LLP

(57) ABSTRACT

A system and method for creating computed tomography (CT) images of a subject imaged with a CT system including acquiring or accessing data that includes or can be transformed into a first sinogram acquired by the CT system without the patient present and a second sinogram acquired by the CT system with the patient present. The method also includes determining a sinogram bias using the first sinogram and the second sinogram, generating a bias image from the CT data using the sinogram bias, and generating an unbiased image of the subject using the bias image and an image produced from the second sinogram.

20 Claims, 7 Drawing Sheets

(56) References Cited

U.S. PATENT DOCUMENTS

| | | | | |
|---|---|---|---|---|
| 2019/0320996 | A1* | 10/2019 | Fetterly | A61B 6/5211 |
| 2021/0217140 | A1* | 7/2021 | Koehler | G06T 5/50 |
| 2023/0326100 | A1* | 10/2023 | Eguizabal | A61B 6/032 382/156 |

OTHER PUBLICATIONS

McCollough et al., "Achieving routine submillisievert ct scanning: Report from the summit on management of radiation dose in ct," Radiology 264(2), pp. 567-580, 2012. PMID: 22692035.

* cited by examiner

SYSTEM AND METHOD FOR CONTROLLING ERRORS IN COMPUTED TOMOGRAPHY NUMBER WITHOUT RAW DETECTOR COUNT DATA

CROSS-REFERENCE TO RELATED APPLICATIONS

N/A

STATEMENT REGARDING FEDERALLY SPONSORED RESEARCH

N/A

BACKGROUND

The present disclosure relates to systems and methods for medical image data preparation, acquisition, and/or reconstruction. More particularly, systems and method are provided for controlling errors in computed tomography (CT) numbers, for example, as can commonly occur at low or reduced radiation dose levels.

In traditional computed tomography systems, an x-ray source projects a beam that is collimated to lie within an X-Y plane of a Cartesian coordinate system, termed the "imaging plane." The x-ray beam passes through the object being imaged, such as a medical patient, and impinges upon an array of radiation detectors. The intensity of the radiation received by each detector element is dependent upon the attenuation of the x-ray beam by the object and each detector element produces a separate electrical signal that relates to the attenuation of the beam. The linear attenuation coefficient is the parameter that describes how the intensity of the x-rays changes when passing through an object. Often, the "mass attenuation coefficient" is utilized because it factors out the dependence of x-ray attenuations on the density of the material. The attenuation measurements from all the detectors are acquired to produce the transmission map of the object.

The source and detector array in a conventional CT system are rotated on a gantry within the imaging plane and around the object so that the projection angle at which the x-ray beam intersects the object constantly changes. A group of x-ray attenuation measurements from the detector array at a given angle is referred to as a "view" and a "scan" of the object. These views are collected to form a set of views made at different angular orientations during one or several revolutions of the x-ray source and detector. In a two dimensional (2D) scan, data is processed to construct an image that corresponds to a 2D slice taken through the object. The prevailing method for reconstructing an image from 2D data is referred to in the art as the filtered back-projection (FBP) technique. This process converts the attenuation measurements from a scan into integers called "CT numbers" or "Hounsfield units", which are used to control the brightness of a corresponding pixel on a display.

Over the past 15 years, much effort has been committed to lowering radiation dose for x-ray CT imaging due to the potential cancer risks associated with the use of ionizing radiation in CT. Many efforts have been made to develop and commercialize systems and methods that enable low-dose CT imaging. Primarily, this has yielded noise-reduction algorithms that seek to reduce the inevitable decreases in SNR as dose is decreased. However, CT hardware with improved radiation dose efficiency, primarily x-ray detectors such as photon counting detectors, have also been studied and developed to enable low dose CT imaging. Photon counting detector CT (PCD-CT) has been featured as one of the most important advances in low dose CT imaging due to its powerful noise rejection functionality in addition to other advantages such as spectral CT imaging capability. Currently, PCD-CT has been developed by major CT manufacturers for preclinical and clinical evaluations. In PCD-CT, the reduction of radiation exposure also helps to alleviate one of the technical challenges, pulse pileup, which is more severe at higher exposure levels.

When the radiation dose in CT imaging is lowered, not only are noise levels and photon starvation noise streaks elevated, but the CT number also becomes more and more inaccurate (i.e., CT numbers are more severely biased when radiation exposure level is reduced). This CT number bias issue has been reported for both regular CT with standard FBP reconstruction and low dose CT with iterative image reconstruction algorithms. For these applications, inaccuracies (i.e. biases) in the CT number can lead to misdiagnosis, mistreatment, and other detrimental clinical consequences.

Despite its noise-reducing capabilities, PCD-CT also faces challenges of inaccurate CT numbers at low-dose levels. With smaller pixel areas and multiple energy channels, the number of digital counts recorded in each bin of each PCD pixel can be as low as single-digit integers, which is orders of magnitude smaller than the digital outputs of typical energy integrating CT detectors. Low PCD counts lead to statistical biases in CT sinograms due to a nonlinear log transformation operation. After tomographic reconstruction, those biases lead to inaccurate CT numbers in PCD-CT images.

The inaccuracy of CT numbers is easily confused with the inaccuracies caused by obvious image artifacts. This is one of the reasons that CT number bias issues are often overlooked in the CT imaging community. It is important to note that CT number bias issues are intrinsically rooted in the statistical nature of photons and the standard image formation process that has been used for the past 50 years in medical CT practices. In the current standard medical CT image formation process, after CT data are acquired, a log-transform is applied to generate the sinogram data, then an image reconstruction algorithm is applied to reconstruct the CT images. However, there is a fundamental flaw in this image formation process. That is, the log-transform itself is a statistically biased estimator, meaning that the statistical mean of the log-transformed data is different from the log-transform of the statistical mean of the data. In other words, different data processing orders (mean-log and log-mean) result in different results.

In medical CT, to avoid excessive radiation dose to patients and to shorten the prolonged data acquisition time, one cannot take the log-mean since there is no statistical mean of the measured patient data available. This constraint in practical medical CT data acquisitions forces us to take the logarithmic transform of the single sample of the measured CT data and then images are reconstructed from the log-transformed sinogram data. Fortunately, this difference is often negligible when the x-ray exposure level is relatively high (i.e. in normal radiation dose CT imaging practices). However, statistical bias becomes exponentially exacerbated in low dose CT imaging and it becomes a factor that must be addressed. Unlike artifact-related issues, for which a plethora of correction methods exist, there is no correction method available to address the statistical bias in standard FBP-based CT images.

Thus, it would be desirable to have systems and methods for managing or overcoming inaccuracy of CT numbers, for example, to improve image quality and/or facilitate dose reductions.

SUMMARY

The present disclosure provides systems and methods that overcome the aforementioned drawbacks by protect against the results of inaccuracies in CT numbers. In one non-limiting example, a system and method is provided for correcting bias in CT data without having access to raw detector count data.

In accordance with one aspect of the disclosure, a method is provided for creating computed tomography (CT) images of a subject imaged with a CT system including acquiring or accessing data that includes or can be transformed into a first sinogram acquired by the CT system without the patient present and a second sinogram acquired by the CT system with the patient present. The method also includes determining a sinogram bias using the first sinogram and the second sinogram, generating a bias image from the CT data using the sinogram bias, and generating an unbiased image of the subject using the bias image and an image produced from the second sinogram.

In accordance with another aspect of the disclosure, a computed tomography system is provided that includes an x-ray source configured to deliver x-rays to an object as the x-ray source is rotated about the object and a detector having a plurality of detector elements configured to receive the x-rays and generate sinogram data therefrom. The system also includes a controller configured to control the x-ray source to deliver the x-rays and to receive the sinogram data from the detector and a processor configured to access, acquire, or derive a first sinogram acquired without the object present between the x-ray source and the detector. The processor is also configured to access, acquire, or derive a second sinogram with the object present between the x-ray source and the detector and determine a sinogram bias using the first sinogram and the second sinogram. The processor is further configured to generate a bias image using the sinogram bias, reconstruct an image of the object from the second sinogram, and generate an unbiased image of the object using the bias image and the image of the object.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION

As described above, CT number bias, particularly in the context of low-dose CT imaging, and further in the context of photon counting CT, is an ongoing problem. To highlight the importance of CT numbers in medical diagnosis, consider the much-desired screening of hepatic steatosis in asymptomatic people as an example. In hepatic steatosis, the medical jargon for fatty liver disease, is of increasing prevalence and is a common finding in the upper abdomen in many populations. In principle, rapid and objective assessment of the liver fat fraction can be achieved by measuring liver CT numbers from low-dose non-contrast chest PCD-CTs for lung cancer screening without requiring a separate liver CT scan. However, the CT number bias issue disqualifies low-dose PCD-CT for reliable liver fat fraction quantification at the moment. Similar concerns about using low-dose PCD-CT for the Bosniak-based cystic renal mass classification require highly accurate CT numbers.

Co-pending U.S. application Ser. No. 17/512,236, filed Oct. 27, 2021, and incorporated herein by reference in its entirety, provides an unbiased sinogram estimator that can address the statistical bias issue in low-dose PCD-CT by using raw detector count data and the systems and processes provided herein. That is, the systems and methods provided in co-pending U.S. application Ser. No. 17/512,236 utilize the original raw PCD counts to correct the CT number bias and generate improved images.

However, in commercial and research PCD system currently available from manufacturers, raw detector counts are hidden from the end-users and, thus, unavailable. Additionally, even if manufactures were inclined to provide access to the raw detector count data or directly implement the systems and methods of U.S. application Ser. No. 17/512,236, some CT systems perform the logarithmic transformation of raw counts as a part of the analog-to-digital conversion (ADC) process for data compression reasons. For those systems, access to the PCD counts is, thus, irretrievably lost. Even the post-log sinogram data are usually not archived for each patient. These practical considerations present challenges to the offline application of CT number bias corrections.

As will be described, the systems and methods provided herein address the statistical bias problem in low-dose CT without requiring the raw detector counts. Bias correction can be achieved using even post-log sinogram data or even the reconstructed, bias-contaminated CT images.

Figure 1:
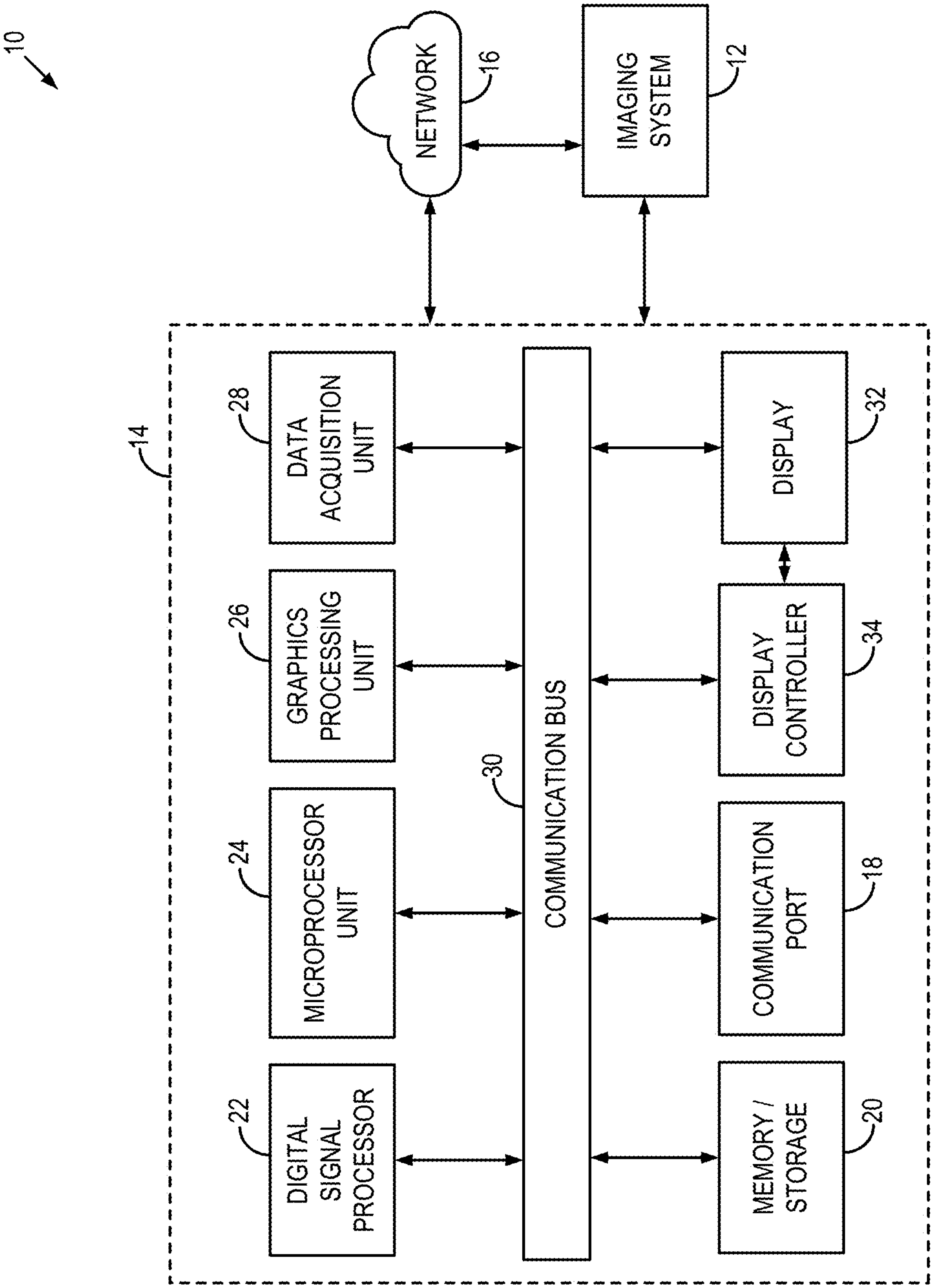
FIG. 1 is a schematic diagram of an example computer system that can be configured to implement the methods described herein.

Referring now to FIG. 1, a block diagram of an example system 10 is provided that can be configured to carry out techniques, methods, and processes accordance with the present disclosure. The system may include an imaging system 12 that is coupled to a computer system 14. The coupling of the imaging system 12 to the computer system 14 may be a direct or dedicated network connection, or may be through a broad network 16, such as an intranet or the Internet.

The computer system 14 may be a workstation integrated with or separate from the medical imaging systems 12 or a variety of other medical imaging systems, including, as non-limiting examples, computed tomography (CT) system, magnetic resonance imaging (MRI) systems, positron emission tomography (PET) systems, single photon emission computed tomography (SPECT) systems, and the like. Furthermore, the computer system 14 may be a workstation integrated within the medical imaging system 12 or may be a separate workstation or mobile device or computing system. To this end, the following description of particular hardware and configurations of the hardware of the example computer system 14 is for illustrative purposes. Some computer systems may have varied, combined, or different hardware configurations.

Medical imaging data acquired by the medical imaging system 12 or other imaging system can be provided to the computer system 14, such as over the network 16 or from a storage device. To this end, the computer system 14 may include a communications port or other input port 18 for communication with the network 16 and system coupled thereto. Also, the computer system 14 may include memory and storage capacity 20 to store and access data or images.

In some configuration, computer system 14 may include one or more processing systems or subsystems. That is, the computer system 14 may include one or more physical or virtual processors. As an example, the computer system 14 may include one or more of a digital signal processor (DSP) 22, a microprocessor unit (MPU) 24, and a graphics processing unit (GPU) 26. If the computer system 14 is integrated into the medical imaging system, a data acquisition unit 28 may be connected directly to the above-described processor(s) 22, 24, 26 over a communications bus 30, instead of communicating acquired data or images via the network 16. As an example, the communication bus 30 can be a group of wires, or a hardwire used for switching data between the peripherals or between any component, such as the communication buses described above.

The computer system 14 may also include or be connected to a display 32. To this end, the computer system 14 may include a display controller 34. The display 32 may be a monitor connected to the computer system 14 or may be integrated with the computer system 14, such as in portable computers or mobile devices.

Figure 2A:
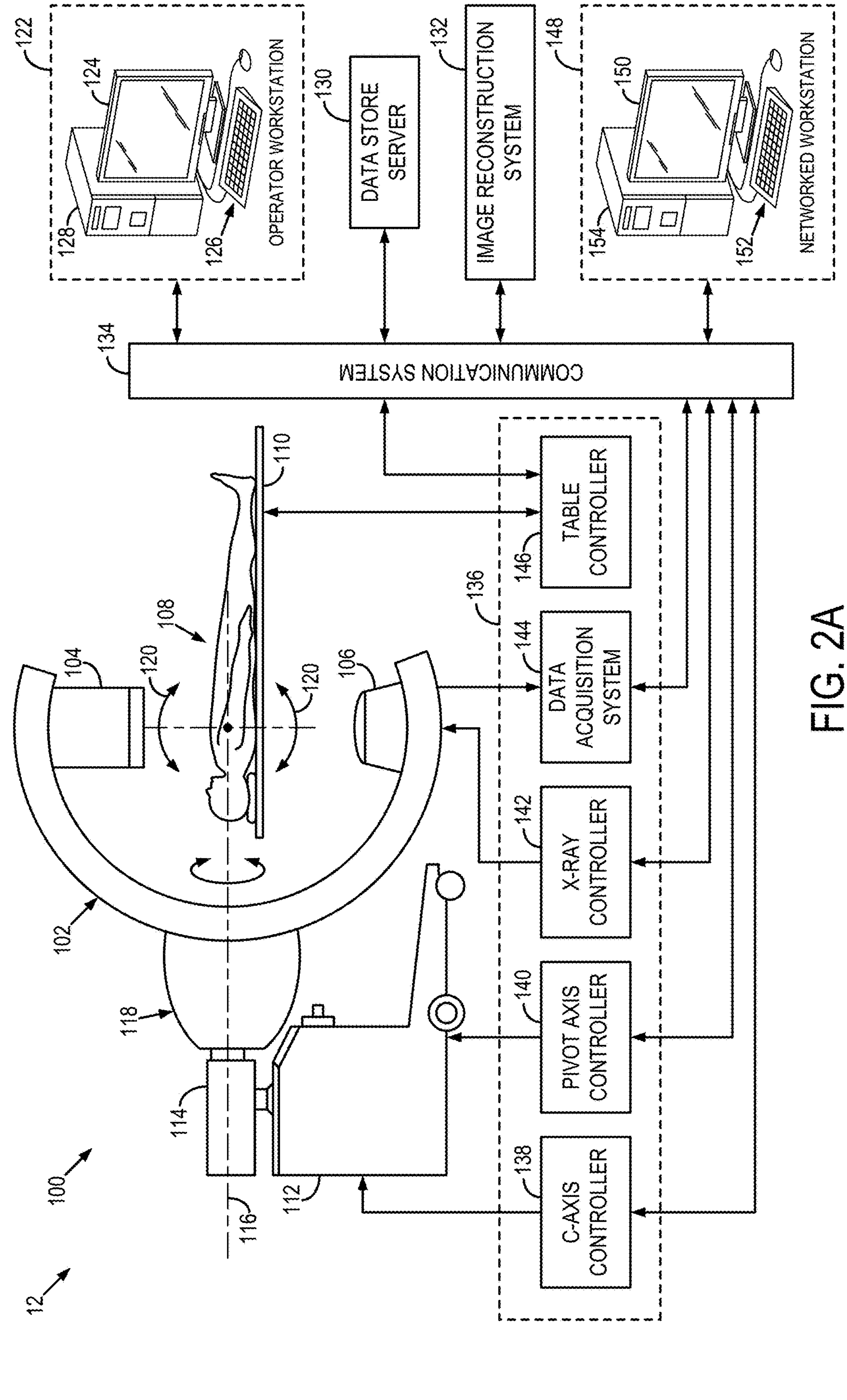
FIG. 2A is a schematic diagram of a C-arm x-ray computed tomography (CT) imaging system configured in accordance with the present disclosure.
Figure 2B:
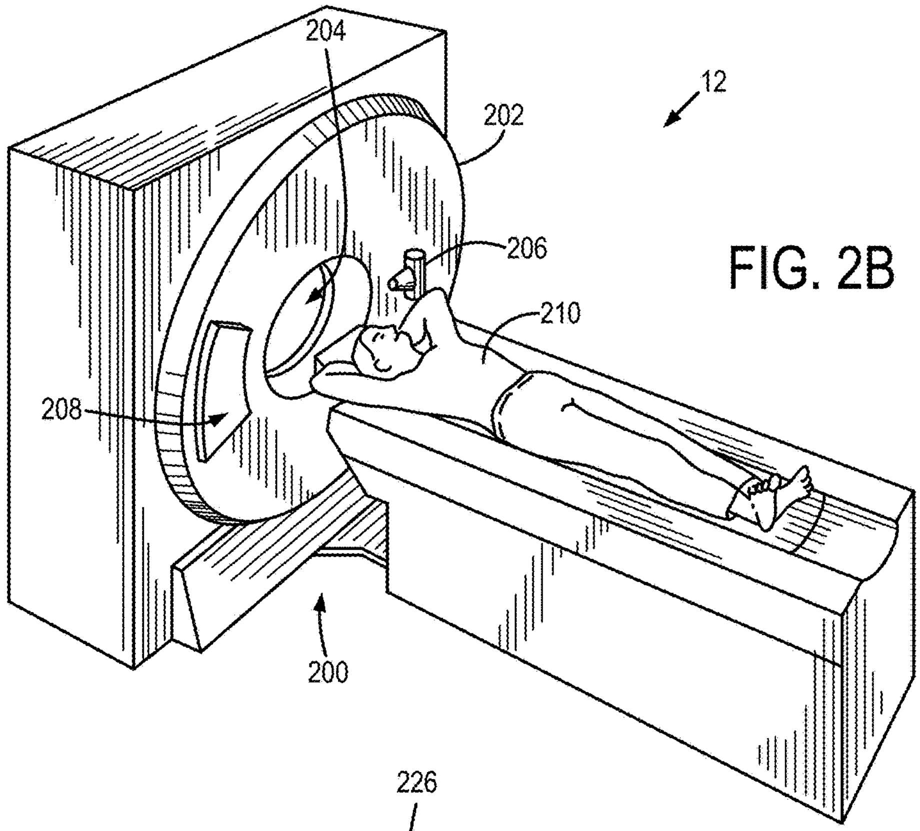
FIG. 2B is a perspective view of an example of an x-ray computed tomography (CT) system.

Referring to FIG. 2A, one, non-limiting example of the imaging system 12 of FIG. 1 is provided. Specifically, in this example, a so-called "C-arm" x-ray imaging system 100 is illustrated for use in accordance with some aspects of the present disclosure. Such an imaging system is generally designed for use in connection with interventional procedures. Such systems stand in contrast to, for example, traditional computed tomography (CT) systems 200, such as illustrated in FIG. 2B, which may also serve as an example of the imaging system 12 of FIG. 1.

Referring again to FIG. 2A, the C-arm x-ray imaging system 100 includes a gantry 102 having a C-arm to which an x-ray source assembly 104 is coupled on one end and an x-ray detector array assembly 106 is coupled at its other end. The gantry 102 enables the x-ray source assembly 104 and detector array assembly 106 to be oriented in different positions and angles around a subject 108, such as a medical patient or an object undergoing examination, which is positioned on a table 110. When the subject 108 is a medical patient, this configuration enables a physician access to the subject 108.

The x-ray source assembly 104 includes at least one x-ray source that projects an x-ray beam, which may be a fan-beam or cone-beam of x-rays, towards the x-ray detector array assembly 106 on the opposite side of the gantry 102. The x-ray detector array assembly 106 includes at least one x-ray detector, which may include a number of x-ray detector elements. The x-ray detector array assembly 1-6 may include a PCD or may include flat panel detectors, such as so-called "small flat panel"

Together, the x-ray detector elements in the one or more x-ray detectors housed in the x-ray detector array assembly 106 sense the projected x-rays that pass through a subject 108. Each x-ray detector element produces an electrical signal that may represent the intensity of an impinging x-ray beam and, thus, the attenuation of the x-ray beam as it passes through the subject 108. In some configurations, each x-ray detector element is capable of counting the number of x-ray photons that impinge upon the detector (i.e., is a PCD). During a scan to acquire x-ray projection data, the gantry 102 and the components mounted thereon rotate about an isocenter of the C-arm x-ray imaging system 100.

The gantry 102 includes a support base 112. A support arm 114 is rotatably fastened to the support base 112 for rotation about a horizontal pivot axis 116. The pivot axis 116 is aligned with the centerline of the table 110 and the support arm 114 extends radially outward from the pivot axis 116 to support a C-arm drive assembly 118 on its outer end. The C-arm gantry 102 is slidably fastened to the drive assembly 118 and is coupled to a drive motor (not shown) that slides the C-arm gantry 102 to revolve it about a C-axis, as indicated by arrows 120. The pivot axis 116 and C-axis are orthogonal and intersect each other at the isocenter of the C-arm x-ray imaging system 100, which is indicated by the black circle and is located above the table 110.

The x-ray source assembly 104 and x-ray detector array assembly 106 extend radially inward to the pivot axis 116 such that the center ray of this x-ray beam passes through the system isocenter. The center ray of the x-ray beam can thus be rotated about the system isocenter around either the pivot axis 116, the C-axis, or both during the acquisition of x-ray attenuation data from a subject 108 placed on the table 110. During a scan, the x-ray source and detector array are rotated about the system isocenter to acquire x-ray attenuation projection data from different angles. By way of example, the detector array is able to acquire thirty projections, or views, per second.

The C-arm x-ray imaging system 100 also includes an operator workstation 122, which typically includes a display 124; one or more input devices 126, such as a keyboard and mouse; and a computer processor 128. The computer processor 128 may include a commercially available programmable machine running a commercially available operating system. The operator workstation 122 provides the operator interface that enables scanning control parameters to be entered into the C-arm x-ray imaging system 100. In general, the operator workstation 122 is in communication with a data store server 130 and an image reconstruction system 132. By way of example, the operator workstation 122, data store server 130, and image reconstruction system 132 may be connected via a communication system 134, which may include any suitable network connection, whether wired, wireless, or a combination of both. As an example, the communication system 134 may include both proprietary or dedicated networks, as well as open networks, such as the Internet.

The operator workstation 122 is also in communication with a control system 136 that controls operation of the C-arm x-ray imaging system 100. The control system 136 generally includes a C-axis controller 138, a pivot axis controller 140, an x-ray controller 142, a data acquisition system (DAS) 144, and a table controller 146. The x-ray controller 142 provides power and timing signals to the x-ray source assembly 104, and the table controller 146 is operable to move the table 110 to different positions and orientations within the C-arm x-ray imaging system 100.

The rotation of the gantry 102 to which the x-ray source assembly 104 and the x-ray detector array assembly 106 are coupled is controlled by the C-axis controller 138 and the pivot axis controller 140, which respectively control the rotation of the gantry 102 about the C-axis and the pivot axis 116. In response to motion commands from the operator workstation 122, the C-axis controller 138 and the pivot axis controller 140 provide power to motors in the C-arm x-ray imaging system 100 that produce the rotations about the C-axis and the pivot axis 116, respectively. For example, a program executed by the operator workstation 122 generates motion commands to the C-axis controller 138 and pivot axis controller 140 to move the gantry 102, and thereby the x-ray source assembly 104 and x-ray detector array assembly 106, in a prescribed scan path.

The DAS 144 samples data from the one or more x-ray detectors in the x-ray detector array assembly 106 and converts the data to digital signals for subsequent processing. For instance, digitized x-ray data are communicated from the DAS 144 to the data store server 130. The image reconstruction system 132 then retrieves the x-ray data from the data store server 130 and reconstructs an image therefrom. The image reconstruction system 130 may include a commercially available computer processor, or may be a highly parallel computer architecture, such as a system that includes multiple-core processors and massively parallel, high-density computing devices. Optionally, image reconstruction can also be performed on the processor 128 in the operator workstation 122. Reconstructed images can then be communicated back to the data store server 130 for storage or to the operator workstation 122 to be displayed to the operator or clinician.

The C-arm x-ray imaging system 100 may also include one or more networked workstations 148. By way of example, a networked workstation 148 may include a display 150; one or more input devices 152, such as a keyboard and mouse; and a processor 154. The networked workstation 148 may be located within the same facility as the operator workstation 122, or in a different facility, such as a different healthcare institution or clinic.

The networked workstation 148, whether within the same facility or in a different facility as the operator workstation 122, may gain remote access to the data store server 130, the image reconstruction system 132, or both via the communication system 134. Accordingly, multiple networked workstations 148 may have access to the data store server 130, the image reconstruction system 132, or both. In this manner, x-ray data, reconstructed images, or other data may be exchanged between the data store server 130, the image reconstruction system 132, and the networked workstations 148, such that the data or images may be remotely processed by the networked workstation 148. This data may be exchanged in any suitable format, such as in accordance with the transmission control protocol (TCP), the Internet protocol (IP), or other known or suitable protocols.

Figure 2C:
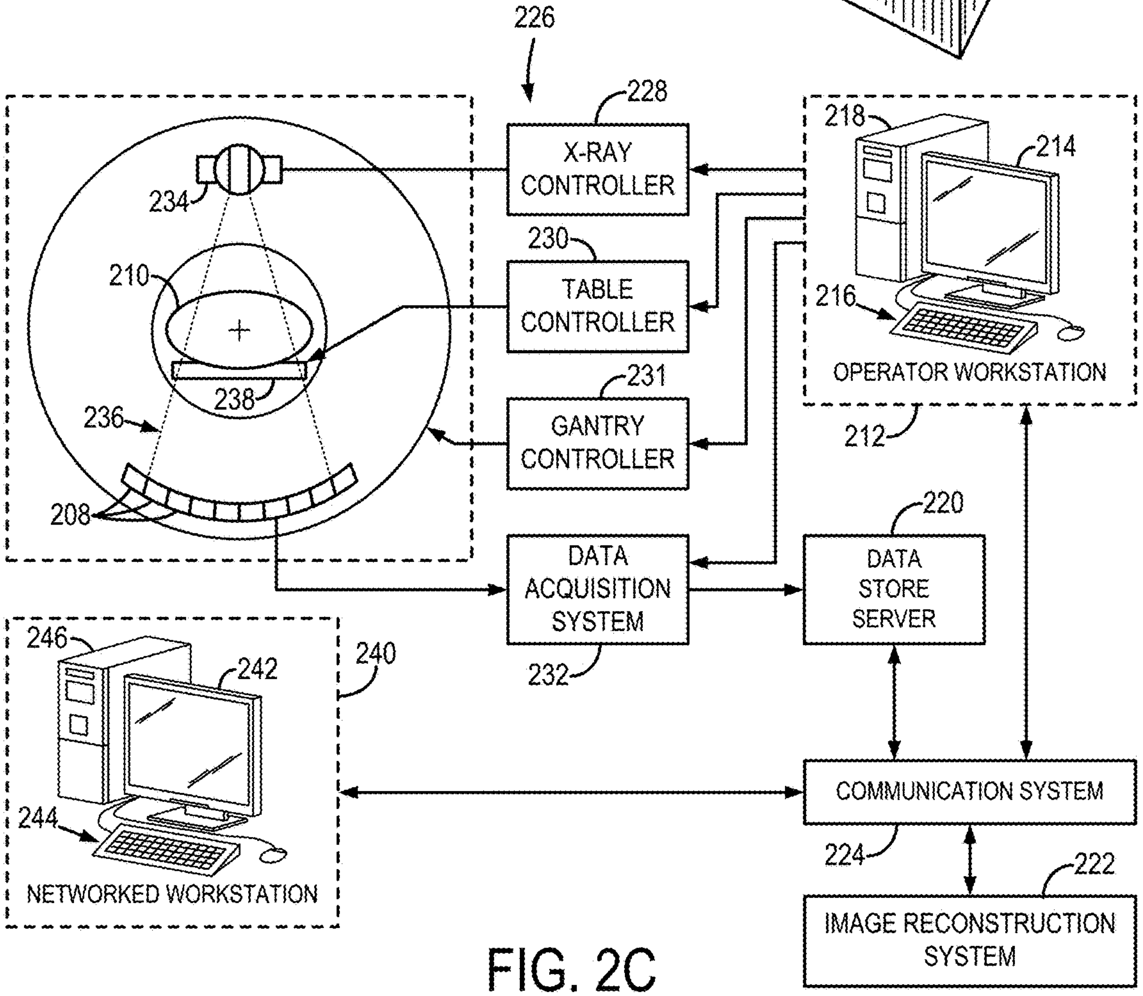
FIG. 2C is a block diagram of CT system, such as illustrated in FIG. 2B.

Similarly, referring to FIGS. 2B and 2C, the imaging system 12 may include a traditional CT system 200, which includes a gantry 202 that forms a bore 204 extending therethrough. In particular, the gantry 202 has an x-ray source 206 mounted thereon that projects a fan-beam, or cone-beam, of x-rays toward a detector array 208 mounted on the opposite side of the bore 204 through the gantry 202 to image the subject 210. Again the detector array 208 may form a PCD.

The CT system 200 also includes an operator workstation 212, which typically includes a display 214; one or more input devices 216, such as a keyboard and mouse; and a computer processor 218. The computer processor 218 may include a commercially available programmable machine running a commercially available operating system. The operator workstation 212 provides the operator interface that enables scanning control parameters to be entered into the CT system 200. In general, the operator workstation 212 is in communication with a data store server 220 and an image reconstruction system 222 through a communication system or network 224. By way of example, the operator workstation 212, data store sever 220, and image reconstruction system 222 may be connected via a communication system 224, which may include any suitable network connection, whether wired, wireless, or a combination of both. As an example, the communication system 224 may include both proprietary or dedicated networks, as well as open networks, such as the Internet.

The operator workstation 212 is also in communication with a control system 226 that controls operation of the CT system 200. The control system 226 generally includes an x-ray controller 228, a table controller 230, a gantry controller 231, and a data acquisition system (DAS) 232. The x-ray controller 228 provides power and timing signals to the x-ray module(s) 234 to effectuate delivery of the x-ray beam 236. The table controller 230 controls a table or platform 238 to position the subject 210 with respect to the CT system 200.

The DAS 232 samples data from the detector 208 and converts the data to digital signals for subsequent processing. For instance, digitized x-ray data are communicated from the DAS 232 to the data store server 220. The image reconstruction system 222 then retrieves the x-ray data from the data store server 220 and reconstructs an image therefrom. The image reconstruction system 222 may include a commercially available computer processor, or may be a highly parallel computer architecture, such as a system that includes multiple-core processors and massively parallel, high-density computing devices. Optionally, image reconstruction can also be performed on the processor 218 in the operator workstation 212. Reconstructed images can then be communicated back to the data store server 220 for storage or to the operator workstation 212 to be displayed to the operator or clinician.

The CT system 200 may also include one or more networked workstations 240. By way of example, a networked workstation 240 may include a display 242; one or more input devices 244, such as a keyboard and mouse; and a processor 246. The networked workstation 240 may be located within the same facility as the operator workstation 212, or in a different facility, such as a different healthcare institution or clinic.

The networked workstation 240, whether within the same facility or in a different facility as the operator workstation 212, may gain remote access to the data store server 220 and/or the image reconstruction system 222 via the communication system 224. Accordingly, multiple networked workstations 240 may have access to the data store server 220 and/or image reconstruction system 222. In this manner, x-ray data, reconstructed images, or other data may be exchanged between the data store server 220, the image reconstruction system 222, and the networked workstations 212, such that the data or images may be remotely processed by a networked workstation 240. This data may be exchanged in any suitable format, such as in accordance with the transmission control protocol (TCP), the Internet protocol (IP), or other known or suitable protocols.

Using the above-described systems, systems and methods are provided for correcting bias in CT data, even without access to raw detector count data. However, before turning to the systems and methods of the present disclosure, it is helpful to consider the basis of the bias problem and correcting the bias using raw detector counts. However, even before turning to these systems and methods, it is advantageous to consider the root cause of bias in CT images. In this explanation, the symbols $(\bar{\cdot})$, E(•), and $\langle \cdot \rangle$ interchangeably to denote the mathematical expectation of a random variable. For example, $\overline{N}_{i0}$ denotes the expected x-ray photon number received by the ith detector element when there is no object present in the x-ray beam (i.e., air scan); $\overline{N}_i$ denotes the actual photon number received by the ith detector element when an image object is present in the beam. Based on the Beer-Lambert law, $\overline{N}_i$ is related to $\overline{N}_{i0}$ and the x-ray linear attenuation coefficient of the image object μ by:

$$\overline{N}_i = \overline{N}_{i0}\int_0^{E_{max}} dE\,\Omega(E)\,e^{-\int_{l_i} dl\mu(\vec{x},E)}; \tag{1}$$

$$= \overline{N}_{i0}\,e^{-\int_{l_i} dl\mu(\vec{x},\epsilon_i)}; \tag{2}$$

where Ω(E) denotes the normalized effective x-ray spectrum, $\epsilon_i \in [0, E_{max}]$, l represents the spatial path of the x-ray, and $\vec{x}$ is the spatial location in the image object. From equation (1) to equation (2), the Mean Value Theorem is used. By taking the logarithmic transform of equation (2), the following well-known fundamental CT imaging equation can be obtained:

$$p_i = \ln\left(\frac{\overline{N}_{i0}}{\overline{N}_i}\right) = \int_{l_i} dl\mu(\vec{x}, \epsilon_i); \tag{3}$$

where $p_i$ is the projection along point, i. As pointed out by both Dr. Cormack and Sir Hounsfield in their 1979 Nobel Lectures, equation (3) has been used to formulate the CT reconstruction problem ever since CT was invented. Despite its wide use, equation (3) has an often overlooked issue. Specifically, this formulation in equation (3) is not intrinsically compatible with clinical CT acquisitions. Note that to get the log-normalized projection data, $p_i$, equation (2) requires the knowledge of both $\overline{N}_{i0}$ and $\overline{N}_i$. While $\overline{N}_{i0}$ can be estimated via a large number of repeated air scans and ensemble averaging, in clinical CT imaging, one cannot repeatedly scan a patient to get $\overline{N}_i$ due to constraints in radiation dose, tube cooling, and clinical throughput. Consequently, one has to rely on a single measurement photon number ($N_i$) to generate the so-called sinogram data, $y_i$, for CT reconstruction:

$$y_i := \ln\left(\frac{\overline{N}_{i0}}{N_i}\right). \tag{4}$$

The replacement of the actual photon number for each detector element with the actual object to be imaged present, $\overline{N}_i$, by a single measurement of photon number, $N_i$ has been implemented in almost all clinical CT scanners for the past 50 years. The inconsistency between the deterministic $p_i$ in equation (3) and the intrinsically stochastic data $y_i$ in equation (4) gives rise to multiple problems. First, there is the well-known noise issue, particularly, when the dose (and, thus, $\overline{N}_i$) is low. Another problem that has been largely overlooked is that $y_i$ is a statistically biased estimator of the desired projection data, $p_i$.

$$\begin{aligned}\langle y_i\rangle &= \ln\overline{N}_{io} - \langle N_i\rangle \\ &\neq p_i = \ln\overline{N}_{io} - \ln\overline{N}_i.\end{aligned} \tag{5}$$

The present disclosure recognizes that the difference between $\langle y_i \rangle$ and $p_i$ is defined as the statistical bias of the sinogram data:

$$\mathrm{Bias}_{y_i} = \langle y_i\rangle - p_i = \ln\bar{N}_i - \langle \ln\bar{N}_i\rangle. \tag{6}$$

For a random variable N that follows the Poisson distribution, its moment-generating function (MGF) is a useful tool to calculate high-order moments. The MGF is given by:

$$M_N(s) := E\{e^{sN}\} = \sum_{n=0}^{\infty} e^{sn} e^{-\lambda}\frac{\lambda^n}{n!} = e^{\lambda[e^s-1]}; \tag{6a}$$

where E{•} denotes mathematical expectation, λ=E{N} denotes the expected value of the random variable N, s is a variable of the MGF that calculates the moments as shown in equation (6b), and n is the index of summation. Using the above MGF, the kth-order moment $N^k$ can be readily calculated by taking the kth-order derivative of the moment generating function with respect to the parameter s at s=0:

$$E\{N^k\} = \left.\frac{d^k M_N(s)}{ds^k}\right|_{s=0}; \tag{6b}$$

Once $E\{N^k\}$ is calculated, the kth-order central moments for $N^k$ can be calculated using the binomial theorem as follows:

$$E\{(N-\lambda)^k\} = \sum_{i=0}^{k}(-1)^{k-i}\frac{k!}{i!(k-i)!}E\{N^i\}\lambda^{k-i}. \tag{6c}$$

The following Table shows the calculated k-th central moments of N for k up to 10.

THE EXPANDED FORM OF E{(N−λ)$^k$} FOR k≤10.

| | |
|---|---|
| E[(N − λ)] | 0 |
| E[(N − λ)$^2$] | λ |
| E[(N − λ)$^3$] | λ |
| E[(N − λ)$^4$] | λ(1 + 3λ) |
| E[(N − λ)$^5$] | λ(1 + 10λ) |
| E[(N − λ)$^6$] | λ(1 + 25λ + 15λ$^2$) |
| E[(N − λ)$^7$] | λ(1 + 56λ + 105λ$^2$) |
| E[(N − λ)$^8$] | λ(1 + 119λ + 490λ$^2$ + 105λ$^3$) |
| E[(N − λ)$^9$] | λ(1 + 246λ + 1918λ$^2$ + 1260λ$^3$) |
| E[(N − λ)$^{10}$] | λ(1 + 501λ + 6825λ$^2$ + 9450λ$^3$ + 945λ$^4$) |

The Taylor series of ln N around N=λ is given by:

$$\begin{aligned}\ln N &= \sum_{i=0}^{\infty}\frac{1}{i!}\frac{d^i(\ln N)}{dN^i}\bigg|_{N=\lambda}(N-\lambda)^i \\ &= \ln\lambda + \sum_{i=1}^{\infty}(-1)^{i+1}\frac{1}{i\lambda^i}(N-\lambda)^i.\end{aligned} \tag{6d}$$

As a result, the statistical bias of ln N can be readily calculated as follows:

$$\begin{aligned}\text{Bias}_{lnN} &:= E\{\ln N\} - \ln E\{N\} \\ &= E\{\ln N\} - \ln\lambda \\ &= \sum_{i=1}^{\infty}(-1)^{i+1}\frac{1}{i\lambda^i}E\{(N-\lambda)^i\}.\end{aligned} \tag{6e}$$

Using the tabulated central moments from the above table, the statistical bias of the random variable ln N is given by:

$$\text{Bias}_{lnN} = -\frac{1}{2\lambda} - \frac{5}{12\lambda^2} - \frac{3}{4\lambda^3} - \frac{251}{120\lambda^4} - \bigcirc\left(\frac{1}{\lambda^5}\right); \tag{6f}$$

where ○ is represents the coefficient for expansion of this series. This result, as will be discussed, can be used to guide construction of unbiased sinogram data. A matter of fact, using equation (6), bias of the CT projection data defined in equation (4) can be calculated using the above result shown in equation (6f) as follows:

$$\begin{aligned}\text{Bias}_{y_i} &= -\text{Bias}_{lnN_i} \\ &= \frac{1}{2\overline{N}_i} + \frac{5}{12\overline{N}_i^2} + \frac{3}{4\overline{N}_i^3} + \frac{251}{120\overline{N}_i^4} + \dots\ .\end{aligned} \tag{7}$$

Equation (7) shows that there exists a bias in the sinogram, if $N_i$ is only measured once and used for CT reconstruction and the magnitude of the bias increases monotonically when radiation dose (a quantity linearly proportional to $\overline{N}_i$) is reduced. When the biased sinogram data are used to reconstruct CT images, it is no surprise to observe bias in CT numbers for both FBP reconstruction and for most of the commercially available statistical model-based iterative reconstruction algorithms.

Though others have recognized this bias problem in CT number, it doesn't seem to indicate a way to solve such a fundamental problem with CT imaging. In its 50-year history, this bias has been present and accepted. For relatively high dose CT imaging, as indicated by the amount of bias shown in equation (7), the resulted CT number bias can be tolerated and accepted in practice, however, in the current movement of low dose CT imaging enabled by both CT scanner hardware and CT image reconstruction algorithms, this statistical bias shown in equation (7) becomes the bottleneck in low dose CT technological development. Without a systematical way to address this challenge, other efforts in low dose CT imaging will not lead to fruitful clinical outcome.

The present disclosure provides systems and methods to overcome this inherent bias problem in CT imaging. As will be described, an unbiased estimator of CT sinogram data can be developed. To develop this unbiased estimator, two additional realizations were utilized. First, the bias of the classical estimator of CT sinogram data (i.e., equation (4), which says $$y_i = \ln\left(\frac{\overline{N}_{i0}}{N_i}\right),$$

consists of a summation of terms, as shown in equation (7)

$$\left(\text{i.e., } \sum_{k=1}^{\infty}\frac{A_k}{N_i^k}\right).$$

Second, the statistical biases of the random variable $$\frac{1}{N_i^k}$$

is also a summation of terms $$\sum_{j=k+1}^{\infty}\frac{B_j}{N_i^j},$$

which has the same functional form as that of the biases of $y_i$ but with different coefficients, $B_j$.

That is, similar to the calculations of statistical bias of ln N, the statistical bias of the random variable $N^{-k}$ can also be calculated as:

$$\begin{aligned}Bias_{N^{-k}} &:= E\{N^{-k}\} - (E\{N\})^{-k} = E\{N^{-k}\} - \lambda^{-k} \\ &= \frac{1}{\lambda^k}E\left\{\left(1+\frac{N-\lambda}{\lambda}\right)^{-k}\right\} - \frac{1}{\lambda^k} \\ &= \frac{1}{\lambda^k}\sum_{i=0}^{\infty}(-1)^i\frac{(k-1+i)!}{i!(k-1)!}E\left\{\left(\frac{N-\lambda}{\lambda}\right)^i\right\} - \frac{1}{\lambda^k} \\ &= \sum_{i=0}^{\infty}\frac{(-1)^i}{\lambda^{i+k}}\frac{(k-1+i)!}{i!(k-1)!}E\{(N-\lambda)^i\}\end{aligned} \tag{7a}$$

Using the above equation (7a) and the results in the table of mean values of Biases in the material basis of images provided below, the statistical bias of the random variable $N^{-k}$ can be readily calculated. The first four are:

$$Bias_{N-1} = \frac{1}{\lambda^2} + \frac{2}{\lambda^3} + \frac{6}{\lambda^4} + O\left(\frac{1}{\lambda^5}\right). \quad (7b)$$

$$Bias_{N-2} = \frac{3}{\lambda^3} + \frac{11}{\lambda^4} + O\left(\frac{1}{\lambda^5}\right)$$

$$Bias_{N-3} = \frac{6}{\lambda^4} + O\left(\frac{1}{\lambda^5}\right)$$

$$Bias_{N-4} = O\left(\frac{1}{\lambda^5}\right)$$

These results were then used to construct the unbiased CT sinogram data described hereafter.

Again, the present disclosure provides builds upon two important recognitions. First, the bias of the classical estimator of CT sinogram data (i.e., equation (4), which says $$y_i = \ln\left(\frac{N_{i0}}{N_i}\right)\right),$$

consists of a summation of terms, as shown in equation (7)

$$\left(\text{i.e., } \sum\nolimits_{k=1}^{\infty} \frac{A_k}{N_i^k}\right).$$

Second, the statistical biases of the random variable $$\frac{1}{N_i^k}$$

is also a summation of terms $$\sum\nolimits_{j=k+1}^{\infty} \frac{B_j}{N_i^j},$$

which has the same functional form as that of the biases of $y_i$ but with different coefficients, $B_j$. These two key observations suggest that it is possible to construct an unbiased estimator for CT projection data as:

$$y_i' = y_i + \sum_{k=1}^{\infty} \frac{C_k}{N_i^k}; \quad (8)$$

where the statistical bias in $y_i$ and the statistical biases of the terms $$\frac{C_k}{N_i^k}$$

in summation can be canceled out provided that the coefficients $C_k$(k=1, 2, . . . ) are properly chosen. In practice, the summation can be truncated at the finite order K to ensure that the residual statistical bias is only up to the higher orders $$O\left(\frac{1}{N_i^{K+1}}\right).$$

As one non-limiting example, consider an explicit construction for the case of K=4. In this case:

$$y_i' = y_i + \frac{C_1}{N_i} + \frac{C_2}{N_i^2} + \frac{C_3}{N_i^3} + \frac{C_4}{N_i^4}. \quad (9)$$

For this estimator constructions, the corresponding statistical bias is given by:

$$\begin{aligned} Bias_{y_i'} &:= \langle y_i' \rangle - p_i = \langle y_i \rangle - p_i + \sum_{k=1}^{4} C_k \left\langle \frac{2}{N_i^k} \right\rangle \\ &= Bias_{y_i} + \sum_{k=1}^{4} C_k \left( \frac{1}{N_i^k} + Bias_{\frac{1}{N_i^k}} \right) \end{aligned}. \quad (10)$$

Using the result of $Bias_{y_i}$ in equation (7) and the calculated statistical biases of terms $$\frac{1}{N_i^k}$$

described above, the statistical bias of the newly constructed estimator of CT sinogram data in equation (9) is given as:

$$\begin{aligned} Bias_{y_i'} = &\left(\frac{1}{2} + C_1\right)\frac{1}{N_i} + \left(\frac{5}{12} + C_1 + C_2\right)\frac{1}{N_i^2} + \\ &\left(\frac{3}{4} + 2C_i + 3C_2 + C_3\right)\frac{1}{N_i^3} + \left(\frac{251}{120} + 6C_1 + 11C_2 + 6C_3 + C_4\right)\frac{1}{N_i^4}. \end{aligned} \quad (11)$$

Therefore, to cancel out the statistical bias in newly constructed CT sinogram data, $$y_i',$$

as shown in equation (9), the coefficients $C_1$, $C_2$, $C_3$, $C_4$ need to be chosen to nullify the coefficients for the terms $$\frac{1}{N_i^k}$$

in equation (11). Recognizing this yields the following choices:

$$\begin{cases} C_1 = -\frac{1}{2}, \\ C_2 = \frac{1}{12}, \\ C_3 = 0, \\ C_4 = -\frac{1}{120}, \end{cases}. \quad (12)$$

The above choices of coefficients allow us to construct, up to the accuracy of $$\mathcal{O}\left(\frac{1}{N_i^5}\right),$$

the unbiased estimator of $p_i$ as follows:

$$y'_i = y_i - \frac{1}{2N_i} + \frac{1}{12N_i^2} - \frac{1}{120N_i^4}. \tag{13}$$

Notably, this is only an example to show the process of how an unbiased estimator of the CT sinogram data can be obtained using the construction scheme presented herein. Other, for example, higher-order constructions can be utilized. As an example, the construction up to the 7th order as follows:

$$y'_i = y_i - \frac{1}{2N_i} + \frac{1}{12N_i^2} + \frac{0}{N_i^3} - \frac{1}{120N_i^4} + \frac{0}{N_i^5} + \frac{1}{252N_i^6}. \tag{14}$$

Thus, though non-limiting example, equations (13) and (14) reflect examples of a new paradigm for CT data. Thus, a first closed-form analytical constructions of unbiased CT sinogram data has been provided to address the statistical bias problem in CT, including low-dose PCD-CT, by using $N_i$ directly. This construct is particularly important as dose is decreased because, as shown above, the magnitude of the correction terms increases with lower radiation dose.

The present disclosure recognizes that, in many practical applications, it may be sufficiently accurate to only keep, for example, the first two terms in the corrected sinogram data, namely:

$$y'_i = y_i - \frac{1}{2N_i} + \frac{1}{12N_i^2}; \tag{15}$$

which will be further detailed below and illustrated with respect to experimental results. Additionally, the two-term approximation in equation (15) is often accurate up to the order of $$\mathcal{O}\left(\frac{1}{N^4}\right)$$

due to the fact that the coefficient of the third order term, $$C_3^i,$$

equals 0 as shown in equation (12).

From equations (7) it follows that:

$$\begin{aligned} \text{Bias}_y &= \langle y\rangle - p = -\langle \ln N\rangle + \ln \overline{N}, \\ &= \frac{1}{2\overline{N}} + \frac{5}{12\overline{N}^2} + \frac{3}{4\overline{N}^3} + \frac{251}{120\overline{N}^4} + \ldots; \end{aligned} \tag{16}$$

After tomographic reconstruction, $\text{Bias}_y$ transforms into CT number biases. To correct for the bias in y, in principle, one can subtract the Laurent series of $\overline{N}$ in equation (16) from y. However, $\overline{N}$ requires repeated measurements and is often unavailable in clinical imaging because $\overline{N}$ is kept as proprietary information by system manufacturers. As illustrated above in equation (13), the sinogram estimator is constructed from N (not $\overline{N}$). It has been shown that y' is unbiased with respect to p.

However, as explained, commercial vendors of clinical CT systems generally do not provide access to raw count data. However, users may be granted access to the post-log sinogram data y in $$y = \ln\left(\frac{\overline{N}_0}{N}\right).$$

In principle, if one knows $\overline{N}_0$, the raw counts N can be calculated from $\overline{N}_0$ and y as follows:

$$N = \overline{N}_0 e^{-y}; \tag{17}$$

which can be inserted into equations (13), (14), or (15) to perform bias correction. However, if N is hidden from the end users or otherwise unavailable, then it can be assumed $\overline{N}_0$ is as well.

With this in mind, the present disclosure provides systems and methods to correct CT number bias without access to the raw count information. In one non-limiting example, a system and method is provided that can estimate $\overline{N}_0$ and N from even post-log sinogram data.

In one non-limiting example, for an air-only (flood field; no subject present) scan, a post-log sinogram is given by:

$$y_{air} = \ln\frac{\overline{N}_0}{N_0}. \tag{18}$$

The Taylor expansion of $y_{air}$ around $\overline{N}_0$ is given by:

$$y_{air} = 0 - \frac{1}{\overline{N}_0}(N_0 - \overline{N}_0) + \frac{1}{2\overline{N}_0^2}(N_0 - \overline{N}_0)^2 + \ldots. \tag{19}$$

Based on equation (19), the variance of $y_{air}$ is related to $\overline{N}_0$ by:

$$\sigma_{y_{air}}^2 = \langle (y_{air} - \langle y_{air}\rangle)^2\rangle \approx \frac{1}{\overline{N}_0} + \frac{3}{2\overline{N}_0^2}. \tag{20}$$

Therefore, $\overline{N}_0$ can be calculated from the variance of $y_{air}$, $$\sigma_{y_{air}}^2.$$

Because $y_{air}$ is the air-scan sinogram, it can be repeatedly acquired M times without worrying about patient radiation exposure. From an ensemble of $y_{air}$, $$\sigma_{y_{air}}^2$$

and $\bar{N}_0$ can be calculated as follows:

$$\sigma^2_{y_{air}} = \frac{1}{M-1}\sum_{i=1}^{M}[(y_{air})_i - \bar{y}_{air}]^2 \Rightarrow \bar{N}_{0,est} \approx \frac{1+\sqrt{1+6\sigma^2_{y_{air}}}}{2\sigma^2_{y_{air}}}. \tag{21}$$

Figure 3:
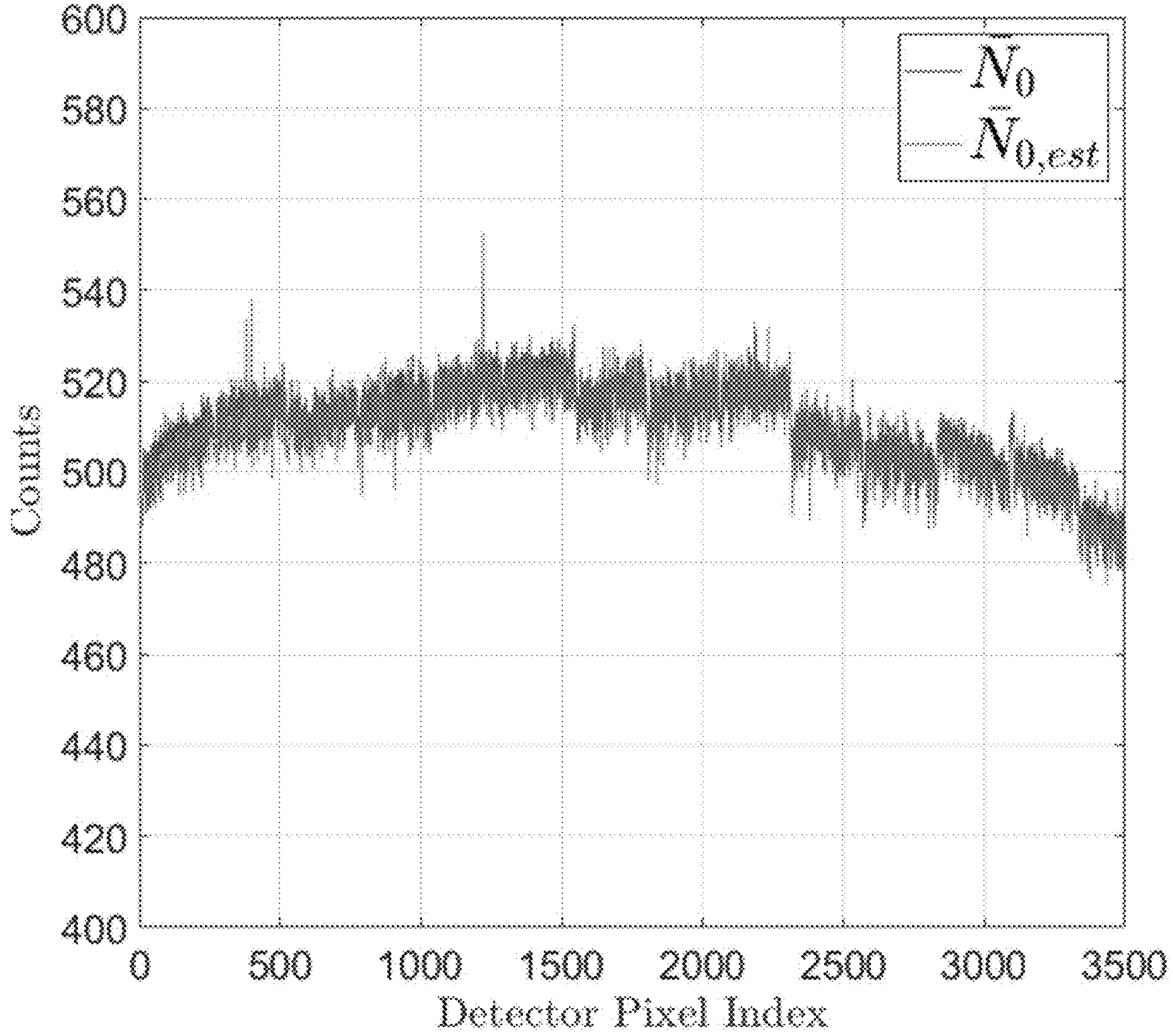
FIG. 3 is a graph showing a comparison of estimated detector count and the actual detector count.

In one non-limiting example, FIG. 3 shows an example of the estimated $$\bar{N}^2_{0,est}$$

and its comparison with the true $\bar{N}_0$.

Once $\bar{N}_0$ is estimated using equation (21), the raw detector counts N can be readily calculated from the sinogram y based on equation (17). For the purpose of bias correction, equation (13) can be re-written as a function of y and $\bar{N}_{0,est}$ as:

$$y' = y - \frac{1}{2}\frac{e^{y}}{\bar{N}_{0,est}} + \frac{1}{12}\frac{e^{2y}}{\bar{N}^2_{0,est}} - \frac{1}{120}\frac{e^{4y}}{\bar{N}^4_{0,est}} + \ldots \tag{22}$$

In current systems, particularly clinical settings, neither raw counts (N) nor post-log sinograms (y) are generally available. When y is lost or never available or when only reconstructed CT images are available, the reconstructed CT image can be denoted as $$\mu'(\vec{x}) = \mu(\vec{x}) + \text{bias}_{\mu}(\vec{x}); \tag{23}$$

where $\text{bias}_\mu$ is usually a few percent of $\mu$ (i.e., tenths of HU). By forward-projecting $\mu'(\vec{x})$, synthesized sinogram can be generated, for example, numerically as:

$$y' = A\mu' = A(\mu + \text{bias}_{\mu}) = p + \Delta p; \tag{24}$$

where A denotes the system matrix, p is the (vectorized) unbiased sinogram defined in equation (3), and $\Delta p$ is the sinogram bias. Since p is unknown, at first glance, it may seem impossible to decouple p and $\Delta p$ based on y' alone. However, the following exponential transform can be used:

$$\bar{N}_0 e^{-y'} = (\bar{N}_0 e^{-p})e^{-\Delta p} = \bar{N}\left[1 - \Delta p + \frac{1}{2}(\Delta p)^2 + \ldots\right]. \tag{25}$$

Because $p = \int dl\,\mu(\vec{x})$ is usually a single-digit dimensionless quantity, $\Delta p$, which is a few percent of p, is much smaller than unity. Therefore, equation (25) can be approximated by:

$$\bar{N}_{0,est}e^{-y'} \approx \bar{N}. \tag{26}$$

Namely, $\bar{N}_{0,est}e^{-y'}$ is a reasonable approximation of $\bar{N}$, even in the presence of biases. Based on equation (16), the sinogram bias can be calculated as follows:

$$\text{bias}_y = \frac{e^{y'}}{2\bar{N}_0} + \frac{5e^{2y'}}{12\bar{N}_0^2} + \frac{3e^{3y'}}{4\bar{N}_0^3} + \frac{251e^{4y'}}{120\bar{N}_0^4} + \ldots \tag{27}$$

Once $\text{bias}_y$ is estimated, it can be used to reconstruct a biased image, which can then be subtracted from the original CT image to create a corrected image, which is mathematically given by:

$$\mu_{corrected} = \mu' - A^{-1}\text{bias}_y. \tag{28}$$

Figure 4:
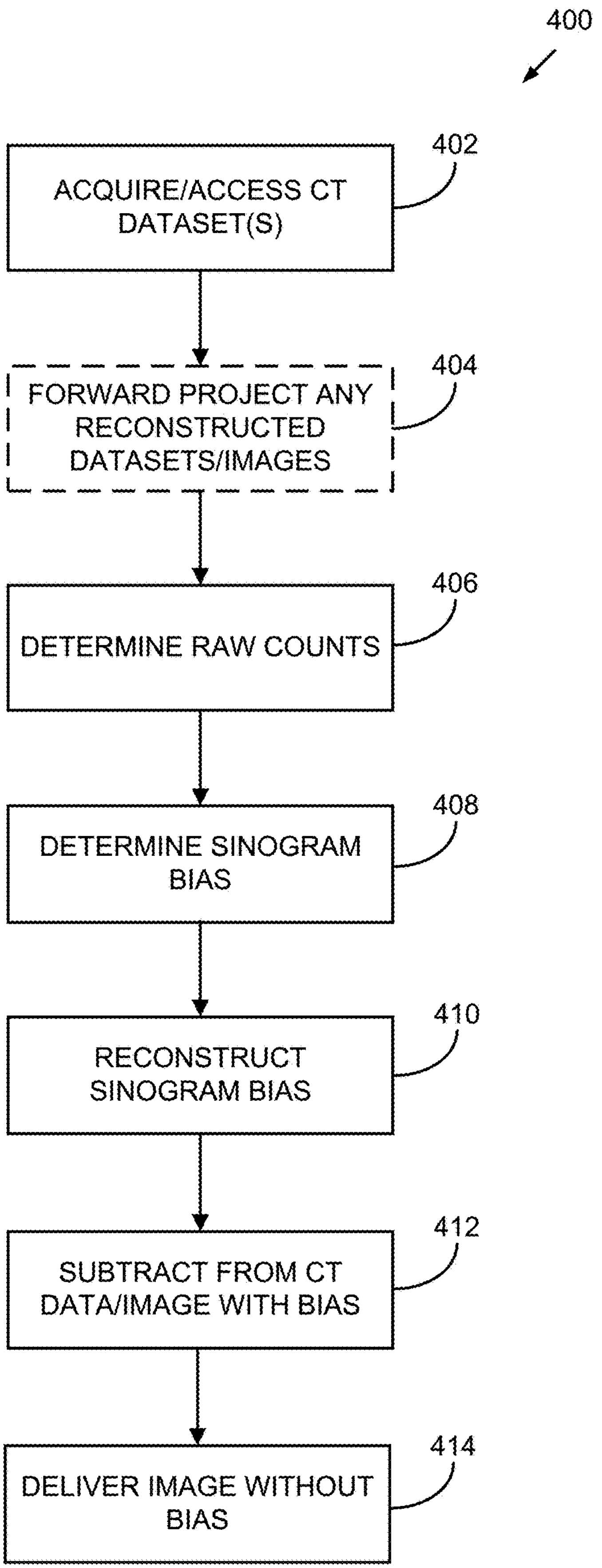
FIG. 4 is a flow chart setting forth some non-limiting example steps of a process for creating unbiased CT images in accordance with the present disclosure.

Referring to FIG. 4, the above-described mathematical construct can be used in an image producing process as follows. That is, one non-limiting example process 400 of applying the constructs and concepts described above begins at process bock 402 by acquiring CT data or accessing previously-acquired CT data. For example, in some situations, sinogram datasets both with patient present and without the patient present are available. In other situations, the sinogram dataset without patient is available (or can be acquired), but the patient-specific sinogram projection data is not available, for example, because only reconstructed images or previously-acquired datasets are available. In this case, process block 402 may include accessing CT datasets that have been reconstructed (e.g., $\mu'(\vec{x})$). If the CT datasets at process block 402 has been reconstructed, at optional process block 404, the reconstructed data or images are forward projected to yield a sinogram (e.g., $\mu'(\vec{x}) \rightarrow y'$). Alternatively, if the datasets are being acquired anew, a sinogram dataset with the patient present may be available. In either case, sinogram datasets without the patient present (i.e., with an empty bore) will be available or can be acquired.

Whether the accessed or acquired datasets are sinogram data or images that were forward projected to sinogram data, at process block 406, equation (25) can be used to derive the raw counts and, at process block 408, determine the sinogram bias, for example, using equation (27). The process then continues by reconstructing the sinogram bias ($\text{bias}_y$) at process block 410 and then subtracting the bias image from the original CT image at process 412. Finally, at process block 414, the image without bias is delivered. These images, which have reduced noise and/or increased signal when compared to traditional images having bias, particularly at lower doses, are produced without knowing the raw detector count data, or even the raw CT data prior to image reconstruction.

EXPERIMENTS

To validate the above-described systems and methods for post-log domain and image domain-based bias correction methods, an experimental PCD-CT system was used. The system has a CdTe-based PCD (XC-Hydra FX50) with 0.1 $mm^2$ pixel size. Other components of the PCD-CT system included a rotating anode tube, an 80 kW high-frequency generator, a square-field manual collimator, and a motorized rotary stage. An anthropomorphic head phantom, a Catphan600 phantom, and a 16 cm Gammex dual-energy CT phantom were imaged. PCD-CT scans were performed at 120 kV with 0.25 mm of copper filtration. 1200 projection views were acquired over a total angular span of 360 degrees for each scan. Each phantom was scanned at different mAs levels ranging from 40 to 320 mAs, which correspond to $CTDI_{vol}$ values ranging from 6 mGy to 48 mGy.

Figure 5:
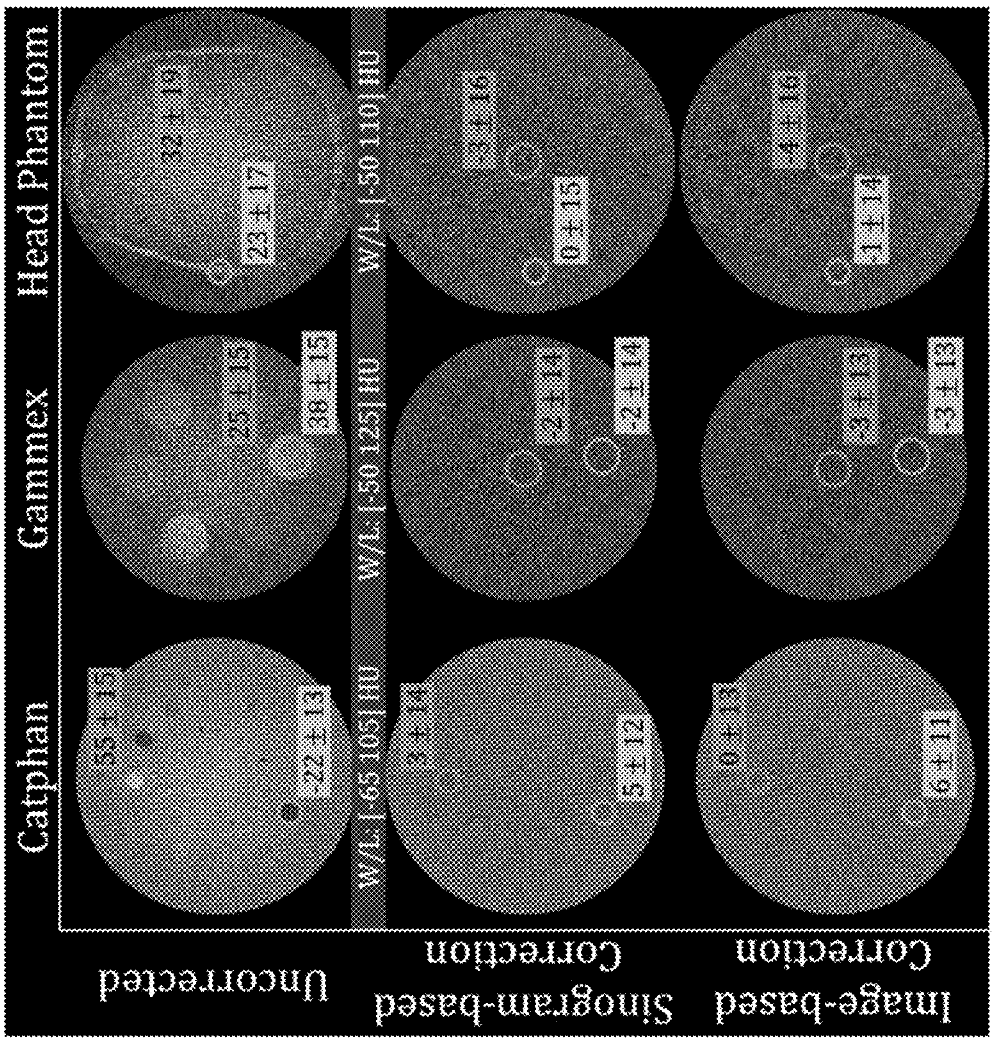
FIG. 5 is a set of correlated images illustrating the difference between the reduce-dose CT images and the standard-dose CT images without statistical biases produced in accordance with the systems and methods of the present disclosure.

To estimate $\overline{N}_0$ without accessing raw detector counts, an air-only (empty) scan was performed with 1200 views. Then, log-normalization was performed using equation (18) to get 1200 sets of $y_{air}$. $\overline{N}_{0,est}$ was calculated from $y_{air}$ using equation (21). Similarly, the post-log sinogram, y, of the test phantoms were corrected for statistical biases my using equation (22) before the FBP algorithm was used to reconstruct the corrected PCD-CT images. FIG. 5 provides a set of difference images generated by subtracting low-dose images with the corresponding high-dose (reference standard) image. The above-described sinogram-based correction was used for the results in the middle row. The above-described image-based correction was used for the results in the third row.

To evaluate the proposed image-based bias correction method, uncorrected low-dose PCD-CT images reconstructed from y were forward-projected to get $y_1$, which was used to estimate $\overline{N}$ and perform bias correction following equations (27) and (28). In all cases, reference standards for p and $\mu(\vec{x})$ were established based on the high dose (48 mGy) data.

Figure 6B:
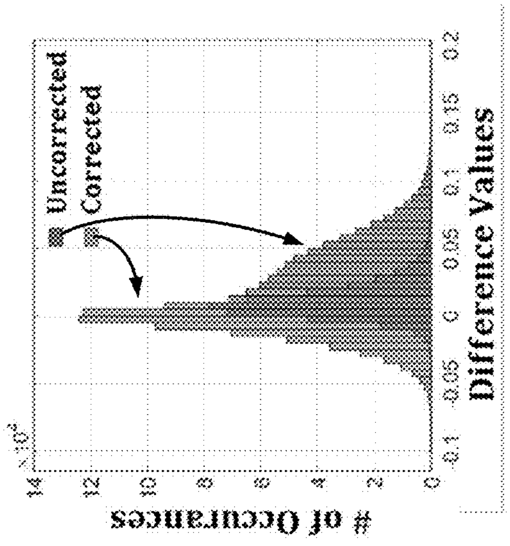
FIG. 6B is a set of histograms showing the difference between the sinograms of FIG. 6A.
Figure 6C:
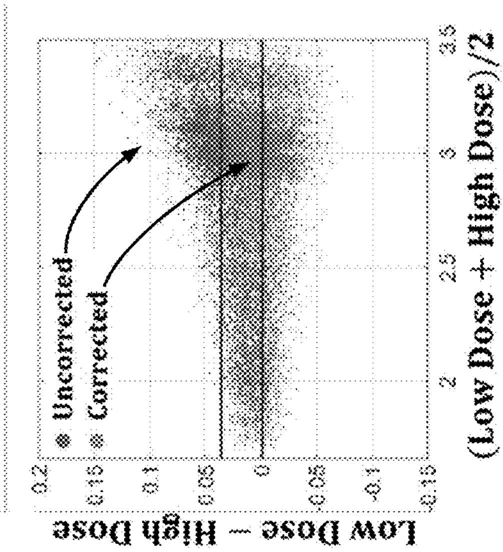
FIG. 6C is a plot showing a Bland-Altman analysis of the sinograms of FIG. 6A
Figure 6A:
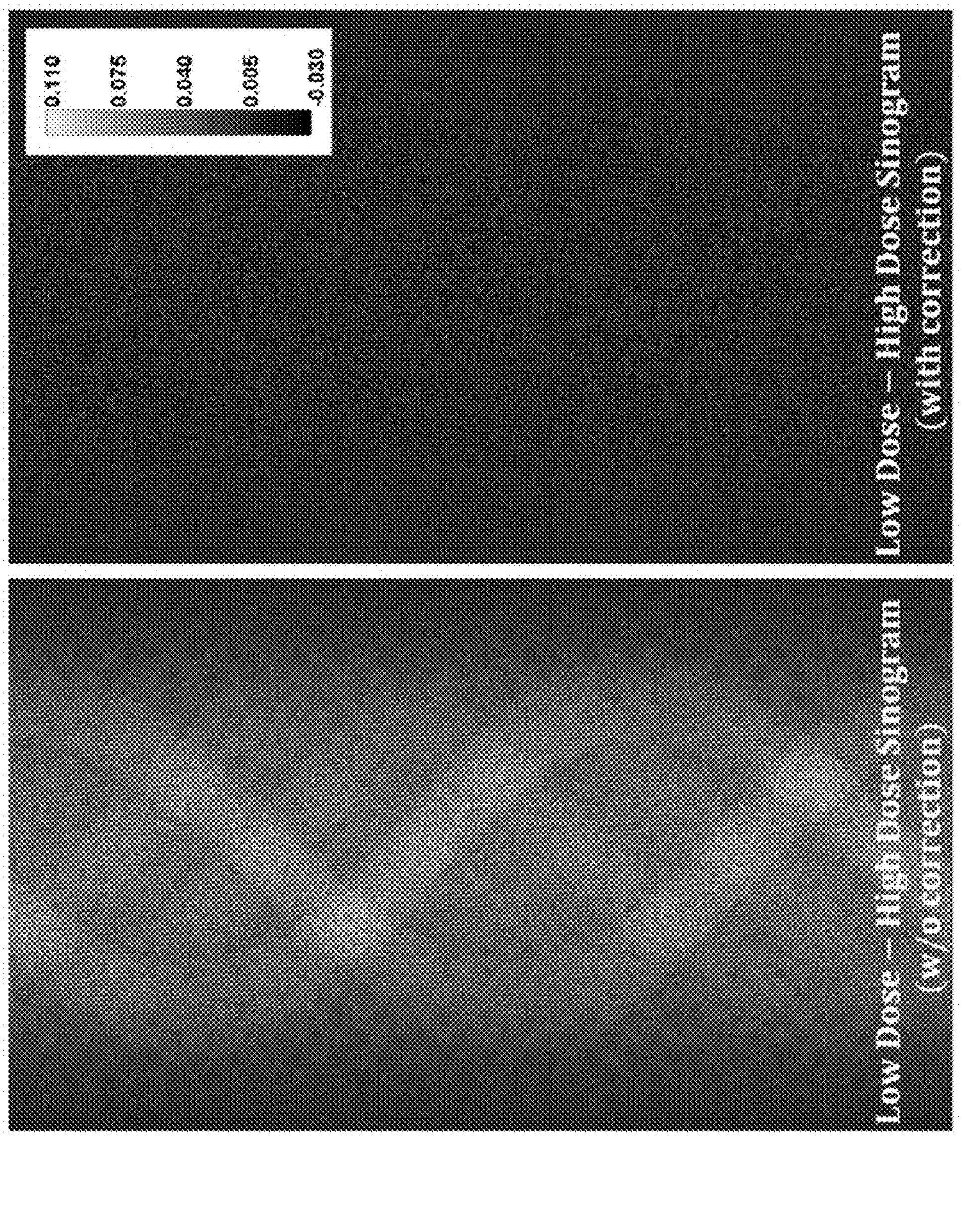
FIG. 6A is a set of sinograms with and without correction in accordance with the present disclosure.

FIG. 6A shows the difference between the reference image p and the uncorrected biased estimator y and corrected estimator $\tilde{y}$. Histograms of the difference between the low-dose sinogram and the reference-standard sinogram are shown in FIG. 6B. The corrected sinogram was calculated using equation (22). A plot of the results of a Bland-Altman analysis of the low-dose sinogram concerning the reference-standard sinogram is provided FIG. 6C. In this way, FIG. 6A demonstrates the difference between the reduced-dose and reference-dose sinogram with and without the proposed bias correction method. Without the proposed correction, there is residual bias, as shown by the insert traces in the difference image and the offset shown in the difference histograms of FIG. 6B and Bland-Altman plot of FIG. 6C. By taking the difference between the low-dose CT images and the high-dose (gold-standard) CT images, the images of FIG. 5 were provided where, for both the sinogram-based method and the image domain-based method, CT number biases had been successfully removed. Additionally, no increase in image noise or spatial blurring was observed in the corrected images.

Due to patient throughput and exposure concerns, $\overline{N}$ has been approximated with N in clinical CT. With the advent of low-dose PCD-CT technology, this substitution has led to appreciable CT number bias in reconstructed images due to the nonlinearity of the logarithmic operation. The systems and methods provided herein provide an analytical correction method for statistical bias correction without the need for raw count data, which is generally unavailable to the end-user. The systems and methods provided herein are able to apply this correction using either post-log sinogram data or the reconstructed PCD-CT image, allowing bias correction to be performed beyond an experimental environment. Results presented show the systems and methods provided herein effectively mitigate bias, allowing low-dose images the same quantification accuracy as standard dose images, while maintaining spatial resolution and noise characteristics.

Therefore, a detailed recognition of the root cause of CT number inaccuracy, particularly, at low dose, is provided. An effective correction method is provided to address this long-standing issue in CT imaging. This correction scheme and its experimental validation are presented in the context of PCD-CT which is one of the most important technologies for routinely achieving sub-millisievert CT scanning. While the reduced noise and improved tissue contrast by photon counting detectors can be exploited to decrease patient radiation dose, the severe CT number inaccuracies at reduced dose levels must be addressed before low-dose PCD-CT can be reliably employed in the clinical practice. As demonstrated by the experimental results, the correction method provided herein not only addresses the CT number bias problem but also improves the material quantification accuracy in spectral PCD-CT images.

As used herein, the phrase "at least one of A, B, and C" means at least one of A, at least one of B, and/or at least one of C, or any one of A, B, or C or combination of A, B, or C. A, B, and C are elements of a list, and A, B, and C may be anything contained in the Specification.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for creating computed tomography (CT) images of a subject imaged with a CT system comprising:
- acquiring or accessing data that includes or can be transformed into a first sinogram acquired by the CT system without the patient present and a second sinogram acquired by the CT system with the patient present;
- determining a sinogram bias using the first sinogram and the second sinogram;
- generating a bias image from the CT data using the sinogram bias; and
- generating an unbiased image of the subject using the bias image and an image produced from the second sinogram.

2. The method of claim 1, wherein the CT system is a photon-counting CT system and the data is photon-counting CT data.

3. The method of claim 1, wherein generating the unbiased image includes subtracting the bias image from the image produced from the second sinogram.

4. The method of claim 1, wherein determining the sinogram bias includes determining an estimate of statistical bias of the second sinogram.

5. The method of claim 1, wherein determining the sinogram bias is performed without raw count data form the CT system or post-log sinograms acquired by the CT system with the patient present.

6. The method of claim 1, wherein acquiring or accessing the data includes forward projecting an image of the patient to form the second sinogram.

7. The method of claim 1, further comprising estimating an actual photon number received by a detector element of the CT system from the data and using an estimated photon number received by a detector element when generating the bias image.

8. The method of claim 7, wherein estimating an actual photon number received is based on an estimate of an expected x-ray photon number received by a detector element of the CT system without the patient present.

9. The method of claim 8, wherein the second sinogram is synthesized by forward-projecting an image reconstructed from data acquired by the CT system with the patient present.

10. The method of claim 7, wherein the actual photon number is estimated as $\overline{N}_{0,est}e^{-y'}$, where $\overline{N}_{0,est}$ is an estimate of $\overline{N}_0$, which is an expected x-ray photon number received by a detector element of the CT system without the patient present, and y' is the second sinogram.

11. A computed tomography system comprising:

an x-ray source configured to deliver x-rays to an object as the x-ray source is rotated about the object;

a detector having a plurality of detector elements configured to receive the x-rays and generate sinogram data therefrom;

a controller configured to control the x-ray source to deliver the x-rays and to receive the sinogram data from the detector;

a processor configured to:

access, acquire, or derive a first sinogram acquired without the object present between the x-ray source and the detector;

access, acquire, or derive a second sinogram with the object present between the x-ray source and the detector;

determine a sinogram bias using the first sinogram and the second sinogram;

generate a bias image using the sinogram bias;

reconstruct an image of the object from the second sinogram; and generate an unbiased image of the object using the bias image and the image of the object.

12. The system of claim 11, wherein the detector includes a photon-counting CT detector array.

13. The system of claim 11, wherein, to generate the unbiased image, the processor is further configured to subtract the bias image from the image of the object.

14. The system of claim 11, wherein, to determine the sinogram bias, the processor is further configured to determine an estimate of statistical bias of the second sinogram.

15. The system of claim 11, wherein, to determine the sinogram bias, the processor is configured to forward project an image of the object to form the second sinogram.

16. The system of claim 11, wherein the processor is further configured to estimate an actual photon number received by a detector element of the detector using an estimated photon number received by a detector element when generating the bias image.

17. The system of claim 16, wherein the processor is further configured to estimate an actual photon number received from the first sinogram.

18. The system of claim 17, wherein the processor is further configured to synthesize the second sinogram by forward-projecting an image reconstructed from data acquired by the CT system with the object present.

19. The system of claim 16, wherein the actual photon number is estimated as $\overline{N}_{0,est}e^{-y'}$, where $\overline{N}_{0,est}$ is an estimate of $\overline{N}_0$, which is an expected x-ray photon number received by a detector element of the CT system without the object present, and y' is the second sinogram.

20. The system of claim 11, wherein the processor is configured to determine the sinogram bias without raw detector counts from the detector.

* * * * *